United States Patent [19]
Isaacs et al.

[11] Patent Number: 6,113,551
[45] Date of Patent: Sep. 5, 2000

[54] SENSORY TESTING DEVICE

[75] Inventors: Judah Isaacs, Oceanside, N.Y.; William Wishner, Indianapolis, Ind.

[73] Assignee: Innovative Premiums, Inc., Oceanside, N.Y.

[21] Appl. No.: 09/148,673

[22] Filed: Sep. 4, 1998

[51] Int. Cl.[7] .................................................. A61B 19/00
[52] U.S. Cl. ........................................ 600/557; 600/587
[58] Field of Search .................................. 600/552, 553, 600/557, 587; 132/321, 323

[56] References Cited

U.S. PATENT DOCUMENTS

| | | | |
|---|---|---|---|
| 3,662,744 | 5/1972 | Low et al. | 600/557 |
| 3,802,445 | 4/1974 | Wesley | 132/321 |
| 4,313,446 | 2/1982 | Kanatani | 600/557 |
| 4,712,572 | 12/1987 | Hovel, III | 132/89 |
| 4,852,728 | 8/1989 | Court | 132/321 |
| 4,986,289 | 1/1991 | McWhorter | 132/323 |
| 5,224,501 | 7/1993 | McKenzie | 132/323 |
| 5,322,077 | 6/1994 | Corella | 132/323 |
| 5,492,132 | 2/1996 | Weinstein et al. | 600/557 |
| 5,823,969 | 10/1998 | Christy | 600/557 |

OTHER PUBLICATIONS

Foot Screening—Care of the Foot in Diabetes; Dept. of Health & Human Services. USA, U.S. Government Print Office: 1994–660–476/00017.

*Primary Examiner*—Cary O'Connor
*Assistant Examiner*—Charles Marmor, IV
*Attorney, Agent, or Firm*—Helgott & Karas, P.C.

[57] ABSTRACT

An economical, diagnostic, sensory testing instrument having a semi-rigid filament rigidly secured within a hand-gripped support for use in the care and treatment of sensory-affecting conditions. The filament is adapted for perpendicular contact with a testing surface, and maintains an outwardly projecting orientation with respect to the support until such contact reaches a predetermined force that causes the filament to buckle.

20 Claims, 2 Drawing Sheets

SENSORY TESTING DEVICE

BACKGROUND OF THE INVENTION

1. Field of the Invention

The present invention relates in general to apparatus for applying a preset pressure to a patient's body, and in particular to an economical diagnostic instrument having a filament laminated within a hand-gripped support for use in the care and treatment of diabetes and other sensory-affecting conditions.

2. Description of Prior Developments

In order to determine the degree to which a patient has lost sensation in a body part such as a hand or foot, doctors have applied localized pressure to the body part to see if the patient can detect the pressure. While some doctors carried out such tests with sharp objects such as pins or pencil points, others found the need for a more standardized measurement.

One such standardized measurement relies on the use of a nylon or plastic monofilament having a known, reproducible buckling stress. By applying an increasing axial force along the filament, with one end of the filament engaged with and perpendicular to the patient's skin, the filament will apply an increasing force on the patient's skin. When the column buckling stress of the filament is reached, the filament will bend sidewardly in an arch as the force and pressure applied to the patient by the filament decreases from a predetermined maximum value.

In this manner, by standardizing the length, diameter and modulus of the filament, a standardized preset maximum force can be repeatedly applied to a patient at the point where the filament initiates buckling. It is known to use a nylon filament standardized to deliver a 10 gram force when applied properly. Diabetic patients who can feel a 10 gram force are not inclined to develop ulcers. Those who cannot feel such a force may require additional medication, treatment or supervision.

Although standardized pressure applicators using nylon filaments are currently known, they are generally bulky and relatively expensive. Such applicators are not particularly well suited for single use or disposable use. Single use or disposable instruments are presently considered by health practitioners to be valuable in limiting the transmission of disease or contamination from one patient to the next.

Accordingly, a need exists for a diagnostic pressure applicator which is economical to produce so as to facilitate single use or disposable use applications.

A further need exists for such an applicator which is constructed from inexpensive components and can be economically disposed after a single use.

Another need exists for such an applicator which can be packaged in an extremely compact flat profile to facilitate shipping, storage, carrying and use.

SUMMARY OF THE INVENTION

The present invention has been developed to fulfill the needs noted above and therefore has as an object the provision of an inexpensive diagnostic instrument for applying a standardized reproducible pressure to a patient's body.

Another object of the invention is the provision of a hand held, lightweight pressure applicator formed of inexpensive, readily available materials including a nylon or plastic pressure-sensitive filament.

Still another object of the invention is the provision of a sensory testing device having a compact planar construction which facilitates bulk packaging, handling and use.

These and other objects are met by the present invention which is directed to a lightweight, easy-to-use, pressure applicator for use in diagnosing patients such as those suffering from diabetes, leprosy or other conditions affecting one's sense of touch and feel. A thin filament or rod of plastic material is laminated between a pair of semi-rigid support sheets. The support sheets may be formed of a single folded sheet of cardboard. The overlapped edges of the folded sheet may be adhesively bonded so as to encapsulate a portion of the filament between the sheets.

A soft rubbery adhesive may also be applied to the encapsulated or laminated portion of the filament to securely anchor and align the filament in position between the sheets. Additional support may be provided to the filament by taping the filament to the inside face of one of the laminating sheets with a strip of adhesive tape.

The aforementioned objects, features and advantages of the invention will, in part, be pointed out with particularity, and will, in part, become obvious from the following more detailed description of the invention, taken in conjunction with the accompanying drawings, which form an integral part thereof.

BRIEF DESCRIPTION OF THE DRAWINGS

In the drawings.

In the various figures of the drawings, like reference characters designate like parts.

DETAILED DESCRIPTION OF THE PREFERRED EMBODIMENTS

The present invention will now be described in connection with the drawings, beginning with FIG. 1 which shows a sensory testing instrument in the form of a pressure applicator 10. Applicator 10 includes a stiff handle or wand 12 formed of a rigid plastic. A fine bore 14 is drilled into one end of the wand 12 for receiving one end of a plastic filament 16. The end of the filament 16 which is inserted into bore 14 may be held in place with an adhesive glue.

Figure 2:
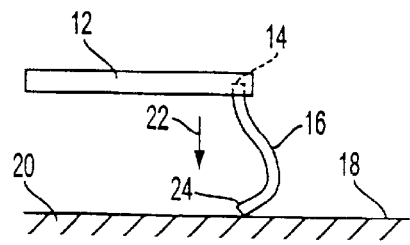
FIG. 2 is a schematic view of the applicator of FIG. 1 applied to a patient's body.

As seen in FIG. 2, filament 16 is aligned normal to the surface 18 of a patient's body part 20. A frequently tested body part is the bottom of a patient's foot and toes. A doctor or other tester applies an axial force 22 along filament 16 with the free end 24 of the filament pressing perpendicularly against surface 18. At a predetermined force 22, the filament 16 buckles thereby relieving a portion of force 22 applied to surface 18 and thereby establishing a maximum applied force and pressure.

This technique is well known and provides a convenient check of the status of a patient's sensory condition. However, the manufacture of applicator 10 is somewhat involved as it requires a boring operation. Moreover, the handle or wand 12 is relatively wide in cross section thereby making compact packaging difficult.

Figure 1:
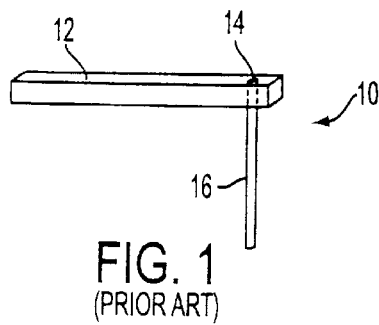
FIG. 1 is a perspective view of a pressure applicator according to the prior art.
Figure 3:
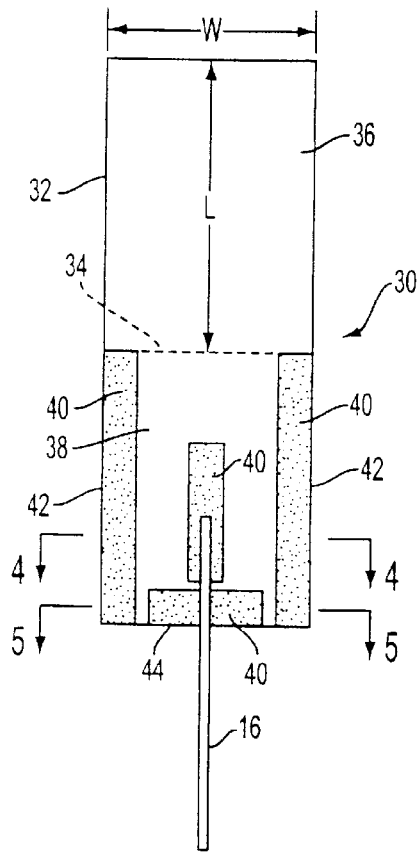
FIG. 3 is a top plan view of a pressure applicator constructed in accordance with the invention at an intermediate point of construction prior to lamination.

In order to simplify and economize the applicator 10 of FIGS. 1 and 2, the present invention, as detailed in FIGS. 3 through 12, has been developed using an inexpensive laminated or layered construction. More particularly, as shown in FIG. 3, a sensory tester in the form of pressure applicator 30 is constructed from a single sheet 32 of inexpensive, semi-rigid material such as thin cardboard. In one embodiment, sheet 32 can have a full length 2 L of about 7 inches, a width W of about 2 inches and a thickness (single ply) of about 0.0125 inches.

Figure 6:
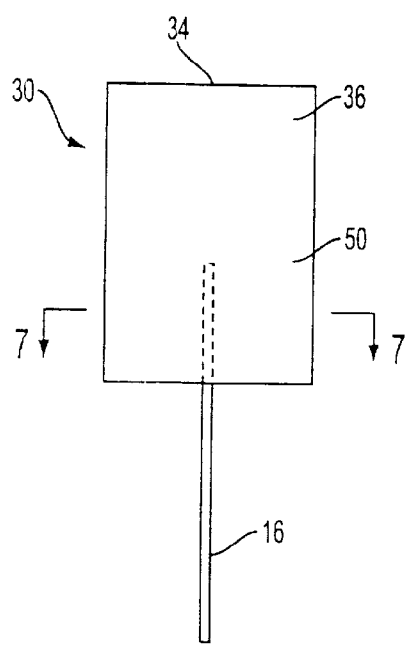
FIG. 6 is a top plan view of the applicator of FIG. 3, in a folded or laminated and fully completed stage of construction.
Figure 4:
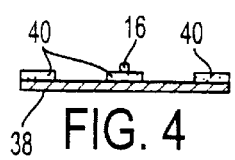
FIG. 4 is a view in section taken through line 4—4 of FIG. 3.
Figure 5:
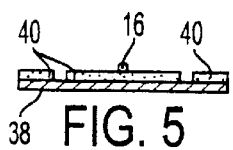
FIG. 5 is a view in section taken through line 5—5 of FIG. 3.

Sheet 32 is folded in half along bend line 34 so as to encapsulate and laminate filament 16 between the folds as shown in FIG. 6. In order to hold the upper sheet or ply 36 in its folded position over the lower sheet or ply 38, a border of adhesive is applied between the rectangular sheets 36, 38 which may be of the same size after folding. As seen in FIG. 3, adhesive in the form of contact cement or double sided adhesive tape is applied in a generally E-shaped or W shaped segmented block pattern on the inner face of lower sheet 38.

One coating or strip 40 of adhesive is applied along each side 42 of the lower sheet 38, one coating or strip 40 of adhesive is applied along the lower edge 44 of the lower sheet 38, and another coating or strip 40 of adhesive is applied in the central portion of the lower sheet 38 to form in a segmented block shape a generally E or W-shaped adhesive pattern. It is also possible to provide adhesive along the border of the upper sheet 36 instead of or in addition to the adhesive applied to the lower sheet 38.

Plastic filament 16, such as a nylon monofilament, is place on the inner face of the lower sheet 38 and aligned substantially parallel with and midway between each side 42 and substantially perpendicular to lower edge 44. Filament 16 is initially held in this centered position by its contact with the center and lower adhesive strips 40. This alignment is shown in more detail in FIGS. 4 and 5.

Filament 16, in the embodiment of FIG. 3, can be about 2¼ inch long and have a diameter of about 0.0175 inch. The free length of filament 16 which extends below lower edge 44 can be about 1.5 inch long. In order to complete the construction of the pressure applicator 30, the upper sheet 36 is folded along bend line 34, as noted above, and pressed into substantially planar adhesive contact with each of the adhesive coatings or strips 40.

Figure 7:
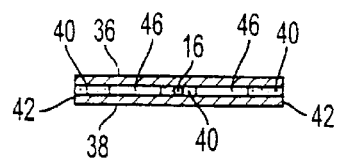
FIG. 7 is a view in section taken through line 7—7 of FIG. 6.
Figure 8:
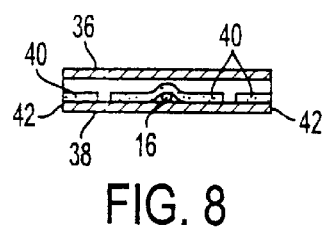
FIG. 8 is an end view of the applicator of FIG. 6 just prior to lamination showing a slightly modified adhesive lamination.
Figure 9:
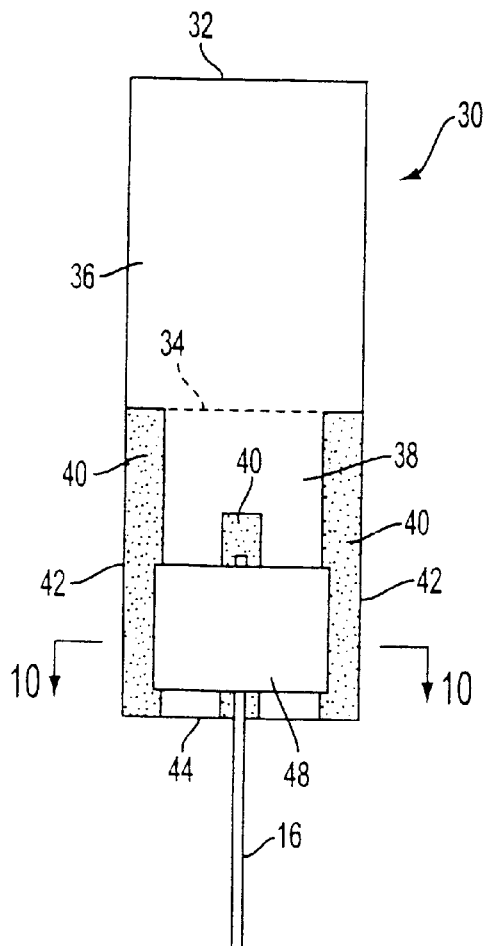
FIG. 9 is a top plan view similar to FIG. 2 showing alternate embodiment of the invention which provides supplemental positive support to a filament.

This pressure tends to at least partially embed the filament 16 into the adhesive, as shown in FIG. 7, so as to securely anchor the filament in place between the upper and lower sheets 36, 38. As seen in FIG. 7, small void spaces 46 may exist between the adhesively bonded portions of sheets 36, 38, but the sheets remain laminated in a substantially planar configuration with filament 16 held coplanar with the sheets.

It is also possible to place the filament 16 directly on the inner face of the lower sheet 38 as shown in FIG. 7 and then apply the central and lower adhesive coatings 40 over the top of the filament 16. The upper sheet 36, shown in a partially open clam-shell configuration in FIG. 7 is then pressed down into pressure contact with each adhesive strip or coating 40. In either case, the folded sheets 36, 38 form a planar gripping handle 50 with filament 16 extending outwardly and substantially coplanar with handle 50.

Another embodiment of the invention is shown in FIGS. 9 through 12 wherein a pressure applicator or sensory tester 30 is constructed substantially the same as that described above except for the use of a supplemental support for holding the filament 16 in an aligned position on the lower sheet 38. This supplemental support can take the form of a strip of single-sided adhesive tape such as clear cellophane adhesive tape 48 shown in FIG. 9. In this case, the lower adhesive strip or coating 40 used in the embodiment of FIGS. 3 and 6 can be omitted.

Figure 11:
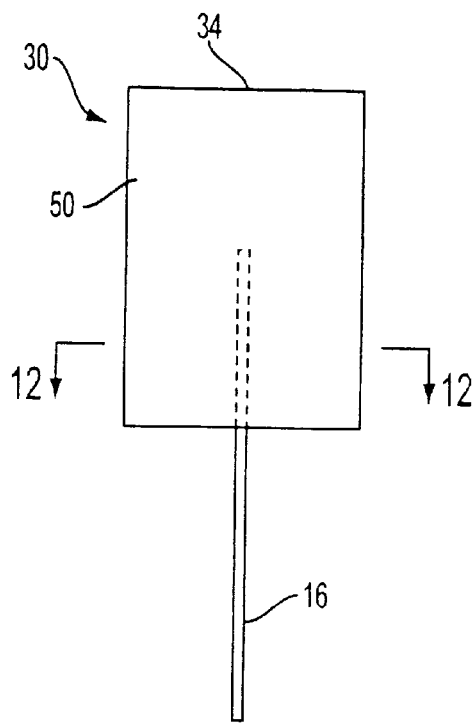
FIG. 11 is a top plan view of the applicator of FIG. 9 in a final completed stage of construction.
Figure 12:
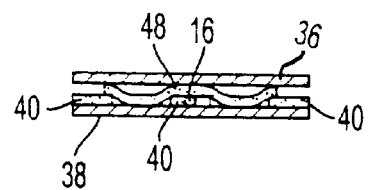
FIG. 12 is a view in section, taken through line 12—12 of FIG. 11.
Figure 10:
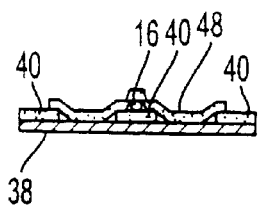
FIG. 10 is a view in section taken through line 10—10 of FIG. 9.

When the upper sheet 36 is folded along bend line 34 and pressed tightly against the lower sheet 38, the filament 16 is pressed and at least partially embedded within the central adhesive strip 40 as seen from a before-and-after lamination comparison of FIGS. 10 and 12. The resulting laminated assembly provides a substantially rectangular two-ply gripping member or handle 50 as shown in FIG. 11.

It is of course possible to use individual, separate upper and lower sheets 36, 38 so as to do away with bending a single sheet 32 along bend line 34. In this case, the filament is simply sandwiched between separate upper and lower sheets. While a segmented adhesive pattern such as the W or E shaped patterns noted above economizes on adhesive, the lower and/or upper sheet or sheets can be completely covered with adhesive or covered with different adhesive patterns.

In addition, while a flat planar rectangular handle 50 is shown, virtually any flat planar shape may be used such as an oval, circular, semi-circular or polygonal shape. Likewise, while taping has been shown, other means of attachment such as glue, staples, or the like can also be used.

There has been disclosed heretofore the best embodiment of the invention presently contemplated. However, it is to be understood that the various changes and modifications may be made thereto without departing from the spirit of the invention.

What is claimed is:

1. A sensory tester, comprising:
    a flat planar handle; and
    a semi-rigid filament connected to said handle, and extending outwardly from and substantially coplanar with said handle, said filament having a first end rigidly held within said handle and a second free end adapted for contact with a testing surface, said filament maintaining a coplanar alignment with the handle until the second end of said filament is exposed to a predetermined force that causes said filament to buckle.

2. The tester of claim 1, wherein said handle comprises a pair of laminated sheets and wherein said filament is held between said sheets.

3. The tester of claim 1, wherein said handle comprises a pair of laminated sheets formed from a single folded sheet.

4. The tester of claim 1, further comprising an adhesive applied to said handle and wherein said filament is at least partially embedded within said adhesive.

5. The tester of claim 1, wherein said handle comprises cardboard.

6. The tester of claim 1, wherein said filament is connected to said handle with adhesive tape.

7. The tester of claim 6, wherein said adhesive tape comprises cellophane tape.

8. The tester of claim 1, wherein said handle has a rectangular shape and said filament is aligned perpendicular to one side of said rectangular shape.

9. The tester of claim 1, wherein said handle comprises a pair of laminated sheets, said filament is laminated between said sheets, and further comprising an adhesive applied in a segmented pattern between said sheets.

10. A sensory tester, comprising:

first and second semi-rigid planar sheets;

an adhesive laminating and bonding said first and second sheets into a handle; and a filament having a first end laminated and rigidly secured between said sheets and a second free end projecting outwardly from said handle and adapted for a forceful contact with a testing surface, which forceful contact causes said filament to buckle.

11. The tester of claim 10, wherein said first and second sheets are substantially the same size.

12. The tester of claim 10, wherein said adhesive defines a segmented pattern between said sheets.

13. The tester of claim 10, wherein said first and second semi-rigid sheets are formed of cardboard.

14. The tester of claim 10, wherein said first and second sheets are formed from a folded sheet of cardboard.

15. The tester of claim 10, wherein said adhesive comprises contact cement contacting said filament.

16. The tester of claim 10, wherein said filament is held adhesively between said sheets.

17. The tester of claim 10, further comprising a strip of tape applied to said filament and to at least one of said sheets for holding said filament on said at least one of said sheets.

18. The tester of claim 17, wherein said tape comprises cellophane tape.

19. The tester of claim 10, wherein said planar sheets are overlapping rectangular sheets.

20. The tester of claim 19, wherein said filament is aligned perpendicular to one edge of each of said rectangular sheets.

* * * * *